US009855281B2

(12) United States Patent
Freeman

(10) Patent No.: US 9,855,281 B2
(45) Date of Patent: Jan. 2, 2018

(54) LIBIDO-ENHANCING THERAPEUTIC AND USE

(71) Applicant: Scott Freeman Consultant, LLC, Las Vegas, NV (US)

(72) Inventor: Scott Freeman, Las Vegas, NV (US)

(73) Assignee: Scott Freeman Consultant, LLC, Las Vegas, NV (US)

( * ) Notice: Subject to any disclaimer, the term of this patent is extended or adjusted under 35 U.S.C. 154(b) by 0 days.

(21) Appl. No.: 15/037,399

(22) PCT Filed: Nov. 20, 2014

(86) PCT No.: PCT/US2014/066532
§ 371 (c)(1),
(2) Date: May 18, 2016

(87) PCT Pub. No.: WO2015/077407
PCT Pub. Date: May 28, 2015

(65) Prior Publication Data
US 2016/0296533 A1 Oct. 13, 2016

Related U.S. Application Data

(60) Provisional application No. 61/906,508, filed on Nov. 20, 2013.

(51) Int. Cl.
*A61K 31/56* (2006.01)
*A61K 31/565* (2006.01)
(Continued)

(52) U.S. Cl.
CPC .......... *A61K 31/565* (2013.01); *A61K 9/0019* (2013.01); *A61K 9/0053* (2013.01);
(Continued)

(58) Field of Classification Search
CPC .. A61K 31/565; A61K 2300/00; A61K 45/06; A61K 9/0019; A61K 9/0053; C07J 15/00; C07J 1/007
See application file for complete search history.

(56) References Cited

U.S. PATENT DOCUMENTS

2002/0183532 A1* 12/2002 Roberts ................ A61K 31/568
552/611
2003/0027804 A1* 2/2003 van der Hoop ........ A61K 31/56
514/177

(Continued)

FOREIGN PATENT DOCUMENTS

EP 1592433 6/2014

OTHER PUBLICATIONS

Written Opinion of the International Searching Authority, dated Feb. 4, 2015 PCT/US14/66532.

(Continued)

*Primary Examiner* — Savitha M Rao
(74) *Attorney, Agent, or Firm* — Kohn & Associates, PLLC

(57) ABSTRACT

A composition for enhancing libido of a pharmaceutically effective amount of a libido-enhancing therapeutic of (5S,10R,13S,17S)-13-methyl-3-oxohexadecahydro-1H-cyclopenta[a]phenanthren-17yl acetate (Formula I), (3S,5S,10R,13S,17S)-3-hydroxy-13-methylhexadecahydro-1H-cyclopenta[a]phenanthren-17yl acetate (Formula II), (5S,10S,13S,17S)-17-hydroxy-13-methyltetradecahydro-1H-cyclopenta[a]phenanthren-3(2H)-one (Formula III), isomers thereof, analogs thereof, or combinations thereof, and a pharmaceutically acceptable carrier. A method of enhancing libido, by administering the composition to an individual in need of an enhanced libido, and enhancing libido in the individual or animal which is male or female. A method of enhancing libido, by administering the composition of the (Continued)

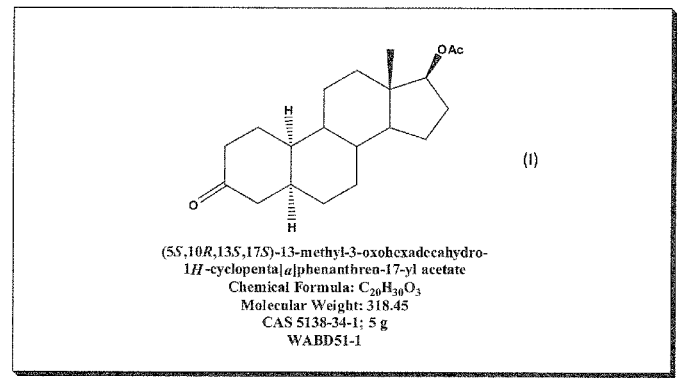

(5S,10R,13S,17S)-13-methyl-3-oxohexadecahydro-
1H-cyclopenta[a]phenanthren-17-yl acetate
Chemical Formula: $C_{20}H_{30}O_3$
Molecular Weight: 318.45
CAS 5138-34-1; 5 g
WABD51-1 present invention to an individual at an age when libido and sexual desire have naturally decreased, and enhancing libido in the individual. A composition for enhancing libido and arousal, including a pharmaceutically effective amount of a libido-enhancing therapeutic in combination with a sexual dysfunction therapeutic. A method of enhancing libido and arousal.

18 Claims, 16 Drawing Sheets

(51) Int. Cl.
A61K 9/00 (2006.01)
C07J 11/00 (2006.01)
A61K 45/06 (2006.01)
C07J 1/00 (2006.01)
C07J 15/00 (2006.01)

(52) U.S. Cl.
CPC .............. *A61K 45/06* (2013.01); *C07J 1/007* (2013.01); *C07J 15/00* (2013.01)

(56) References Cited

U.S. PATENT DOCUMENTS

| | | | |
|---|---|---|---|
| 2004/0224884 A1* | 11/2004 | Manolagas | A61K 31/00 514/44 R |
| 2004/0260092 A1* | 12/2004 | Miller | C07C 231/12 546/2 |
| 2005/0136140 A1* | 6/2005 | Chou | A61K 31/19 424/757 |
| 2005/0245539 A1 | 11/2005 | Mendla | |

OTHER PUBLICATIONS

Comparison of the Receptor Binding Properties of Nandrolone and Testosterone Under in Vitro and in Vivo Conditions, E.W. Bergink, J. steroid Biochem, vol. 22, No. 6, 1985, pp. 831-836.

Successful in Silico Discovery of Novel Nonsteroidal Ligands for Human Sex Hormone Binding Globulin, Artem Cherkasov, J. Med. Chem., 2005, 43, pp. 3203-3213.

An Updated Steroid Benchmark Set and Its Application in the Discovery of Novel Nanomolar Ligands of Sex Hormone-Binding Globulin, Artem Cherkasov, J. Med. Chem., 2008, 51, pp. 2047-2056.

Steroid Structural Requirements for High Affinity Binding to Human Sex Steroid Binding Protein (SBP), G. R. Cunningham, Steroids, Sep. 1981, vol. 38, No. 3.

Metabolism of 19-Nortestosterone by Human Prostate, Wells E. Farnsworth.

3-Hydroxy Steroid Dehydrogenase Activities of Cortisone Reductase, William Gibb, Biochem. J., 1973, 135, pp. 881-888.

Formation of 5a steroids by biotransformation involving the 5a-reductase activity of Penicillium decumbens, Herbert Holland, Steroids, 1994, vol. 59, Nov.

Comparison between steroid binding to membrane progesterone receptor a (mPRa) and to nuclear progesterone receptor: Correlation with physicochemical properties assessed by comparative molecular field analysis and identification of mPRa-specific agonists, Jan Kelder, Steroids 75 (2010, pp. 314-322.

7a-methyl-19-nortestosterone, a synthetic androgen with high potency: structure-activity comparisons with other androgens; N. Kumar, Journal of Steroid Biochemistry & Molecular Biology 71, 1999, pp. 213-222.

5a-Reduction of Norethisterone Enhances its Binding Affinity for Androgen Receptors but Diminishes its Androgenic Potency, Ana E. Lemus, J. Steroid Biochem. Molec. Biol. vol. 60, No. 1-2, 1997, pp. 121-129.

Steroid Structure and Androgenic Activity: Specificities Involved in the Receptor Binding and Nuclear Retention of Various Androgens, Shutsung Liao, The Journal of Biological Chemistry, 1973, 248, pp. 6154-6162.

Electrophilicity index as a possible descriptor of biological activity, R. Parthasarathi, Bloorganic & Medicinal Chemistry 12, 2004, pp. 5533-5543.

Further Studies of the Specificity of the Sex Hormone-Binding Globulin of Human Plasma, Beverley E. Pearson Murphy.

Searching for the physiological function of 17B-hydroxysteroid dehydrogenase from the fungus Cochlioboius lunatus: studies of substrate specificity and expression analysis, T, Lanisnik. Rizner, Molecular and Cellular Endocrinology 171, 2001, pp. 193-193.

Anabolic Steriods: Side Effects, Harm Kuipers, Encyclopedia of Sports Medicine and Science, 1998.

* cited by examiner

| Model | Result | Probability |
|---|---|---|
| Absorption | | |
| Blood-Brain Barrier | BBB+ | 0.9606 |
| Human Intestinal Absorption | HIA+ | 1.0000 |
| Caco-2 Permeability | Caco2+ | 0.8764 |
| P-glycoprotein Substrate | Substrate | 0.6517 |
| P-glycoprotein Inhibitor | Non-inhibitor | 0.5165 |
| P-glycoprotein Inhibitor | Non-inhibitor | 0.9069 |
| Renal Organic Cation Transporter | Non-inhibitor | 0.7054 |
| Distribution | | |
| Metabolism | | |
| CYP450 2C9 Substrate | Non-substrate | 0.7836 |
| CYP450 2D6 Substrate | Non-substrate | 0.9018 |
| CYP450 3A4 Substrate | Substrate | 0.7424 |
| CYP450 1A2 Inhibitor | Non-inhibitor | 0.8304 |
| CYP450 2C9 Inhibitor | Non-inhibitor | 0.9319 |
| CYP450 2D6 Inhibitor | Non-inhibitor | 0.9516 |
| CYP450 2C19 Inhibitor | Inhibitor | 0.5073 |
| CYP450 3A4 Inhibitor | Non-inhibitor | 0.9088 |
| CYP Inhibitory Promiscuity | Low CYP Inhibitory Promiscuity | 0.8700 |
| Excretion | | |
| Toxicity | | |
| Human Ether-a-go-go-Related Gene Inhibition | Weak inhibitor | 0.8616 |
| | Non-inhibitor | 0.7227 |
| AMES Toxicity | Non AMES toxic | 0.9353 |
| Carcinogens | Non-carcinogens | 0.9534 |
| Fish Toxicity | High FHMT | 0.9851 |
| Tetrahymena Pyriformis Toxicity | High TPT | 0.9340 |
| Honey Bee Toxicity | High HBT | 0.8288 |
| Biodegradation | Not ready biodegradable | 0.9013 |

FIGURE 5A

| Model | Value | Unit |
|---|---|---|
| Absorption | | |
| Aqueous solubility | -4.3858 | LogS |
| Caco-2 Permeability | 1.8536 | LogPapp, cm/s |
| Distribution | | |
| Metabolism | | |
| Excretion | | |
| Toxicity | | |
| Rat Acute Toxicity | 1.6594 | LD50, mol/kg |
| Fish Toxicity | 0.5111 | pLC50, mg/L |
| Tetrahymena Pyriformis Toxicity | 0.6377 | pIGC50, ug/L |

FIGURE 5B

| Model | Result | Probability |
|---|---|---|
| Absorption | | |
| Blood-Brain Barrier | BBB+ | 0.9773 |
| Human Intestinal Absorption | HIA+ | 1.0000 |
| Caco-2 Permeability | Caco2+ | 0.7182 |
| P-glycoprotein Substrate | Non-substrate | 0.5065 |
| P-glycoprotein Inhibitor | Inhibitor | 0.6929 |
| | Non-inhibitor | 0.6643 |
| Renal Organic Cation Transporter | Non-inhibitor | 0.7816 |
| Distribution | | |
| Metabolism | | |
| CYP450 2C9 Substrate | Non-substrate | 0.8245 |
| CYP450 2D6 Substrate | Non-substrate | 0.9158 |
| CYP450 3A4 Substrate | Substrate | 0.6714 |
| CYP450 1A2 Inhibitor | Non-inhibitor | 0.9491 |
| CYP450 2C9 Inhibitor | Non-inhibitor | 0.9043 |
| CYP450 2D6 Inhibitor | Non-inhibitor | 0.9663 |
| CYP450 2C19 Inhibitor | Non-inhibitor | 0.8802 |
| CYP450 3A4 Inhibitor | Non-inhibitor | 0.8834 |
| CYP Inhibitory Promiscuity | Low CYP Inhibitory Promiscuity | 0.9553 |
| Excretion | | |
| Toxicity | | |
| Human Ether-a-go-go-Related Gene Inhibition | Weak inhibitor | 0.9443 |
| | Non-inhibitor | 0.7300 |
| AMES Toxicity | Non AMES toxic | 0.9680 |
| Carcinogens | Non-carcinogens | 0.9036 |
| Fish Toxicity | High FHMT | 0.9854 |
| Tetrahymena Pyriformis Toxicity | High TPT | 0.8574 |
| Honey Bee Toxicity | High HBT | 0.8067 |
| Biodegradation | Not ready biodegradable | 0.9736 |

ADMET Predicted Profile --- Classification

FIGURE 6A

ADMET Predicted Profile --- Regression

| Model | Value | Unit |
|---|---|---|
| Absorption | | |
| Aqueous solubility | -4.7174 | LogS |
| Caco-2 Permeability | 1.1294 | LogPapp, cm/s |
| Distribution | | |
| Metabolism | | |
| Excretion | | |
| Toxicity | | |
| Rat Acute Toxicity | 1.6933 | LD50, mol/kg |
| Fish Toxicity | 0.2959 | pLC50, mg/L |
| Tetrahymena Pyriformis Toxicity | 1.0948 | pIGC50, ug/L |

FIGURE 6B

| Model | Result | Probability |
|---|---|---|
| Absorption | | |
| Blood-Brain Barrier | BBB+ | 0.9641 |
| Human Intestinal Absorption | HIA+ | 0.9968 |
| Caco-2 Permeability | Caco2+ | 0.7619 |
| P-glycoprotein Substrate | Substrate | 0.6157 |
| P-glycoprotein Inhibitor | Inhibitor | 0.5118 |
| | Non-inhibitor | 0.8222 |
| Renal Organic Cation Transporter | Non-inhibitor | 0.8143 |
| Distribution | | |
| Metabolism | | |
| CYP450 2C9 Substrate | Non-substrate | 0.7815 |
| CYP450 2D6 Substrate | Non-substrate | 0.9346 |
| CYP450 3A4 Substrate | Substrate | 0.7105 |
| CYP450 1A2 Inhibitor | Non-inhibitor | 0.8828 |
| CYP450 2C9 Inhibitor | Non-inhibitor | 0.8736 |
| CYP450 2D6 Inhibitor | Non-inhibitor | 0.9722 |
| CYP450 2C19 Inhibitor | Non-inhibitor | 0.8679 |
| CYP450 3A4 Inhibitor | Non-inhibitor | 0.8772 |
| CYP Inhibitory Promiscuity | Low CYP Inhibitory Promiscuity | 0.9694 |
| Excretion | | |
| Toxicity | | |
| Human Ether-a-go-go-Related Gene Inhibition | Weak inhibitor | 0.9743 |
| | Non-inhibitor | 0.6498 |
| AMES Toxicity | Non AMES toxic | 0.9481 |
| Carcinogens | Non-carcinogens | 0.9344 |
| Fish Toxicity | High FHMT | 0.9731 |
| Tetrahymena Pyriformis Toxicity | High TPT | 0.9775 |
| Honey Bee Toxicity | High HBT | 0.8142 |
| Biodegradation | Not ready biodegradable | 0.9707 |

ADMET Predicted Profile --- Classification

FIGURE 7A

ADMET Predicted Profile --- Regression

| Model | Value | Unit |
|---|---|---|
| Absorption | | |
| Aqueous solubility | -4.5756 | LogS |
| Caco-2 Permeability | 1.2529 | LogPapp, cm/s |
| Distribution | | |
| Metabolism | | |
| Excretion | | |
| Toxicity | | |
| Rat Acute Toxicity | 2.0714 | LD50, mol/kg |
| Fish Toxicity | 1.1438 | pLC50, mg/L |
| Tetrahymena Pyriformis Toxicity | 1.1164 | pIGC50, ug/L |

FIGURE 7B

| Model | Result | Probability |
|---|---|---|
| Absorption | | |
| Blood-Brain Barrier | BBB+ | 0.9738 |
| Human Intestinal Absorption | HIA+ | 1.0000 |
| Caco-2 Permeability | Caco2+ | 0.8660 |
| P-glycoprotein Substrate | Substrate | 0.5719 |
| P-glycoprotein Inhibitor | Non-inhibitor | 0.6115 |
| | Non-inhibitor | 0.8708 |
| Renal Organic Cation Transporter | Non-inhibitor | 0.7662 |
| Distribution | | |
| Metabolism | | |
| CYP450 2C9 Substrate | Non-substrate | 0.7328 |
| CYP450 2D6 Substrate | Non-substrate | 0.9173 |
| CYP450 3A4 Substrate | Substrate | 0.6970 |
| CYP450 1A2 Inhibitor | Non-inhibitor | 0.6103 |
| CYP450 2C9 Inhibitor | Non-inhibitor | 0.9054 |
| CYP450 2D6 Inhibitor | Non-inhibitor | 0.9745 |
| CYP450 2C19 Inhibitor | Non-inhibitor | 0.8782 |
| CYP450 3A4 Inhibitor | Non-inhibitor | 0.8770 |
| CYP Inhibitory Promiscuity | Low CYP Inhibitory Promiscuity | 0.9684 |
| Excretion | | |
| Toxicity | | |
| Human Ether-a-go-go-Related Gene Inhibition | Weak inhibitor | 0.9292 |
| | Non-inhibitor | 0.5916 |
| AMES Toxicity | Non AMES toxic | 0.9391 |
| Carcinogens | Non-carcinogens | 0.9286 |
| Fish Toxicity | High FHMT | 0.9517 |
| Tetrahymena Pyriformis Toxicity | High TPT | 0.9334 |
| Honey Bee Toxicity | High HBT | 0.7485 |
| Biodegradation | Not ready biodegradable | 0.9593 |

ADMET Predicted Profile --- Classification

FIGURE 8A

ADMET Predicted Profile --- Regression

| Model | Value | Unit |
|---|---|---|
| Absorption | | |
| Aqueous solubility | -4.3005 | LogS |
| Caco-2 Permeability | 1.7950 | LogPapp, cm/s |
| Distribution | | |
| Metabolism | | |
| Excretion | | |
| Toxicity | | |
| Rat Acute Toxicity | 1.9534 | LD50, mol/kg |
| Fish Toxicity | 1.3171 | pLC50, mg/L |
| Tetrahymena Pyriformis Toxicity | 0.5321 | pIGC50, ug/L |

FIGURE 8B

LIBIDO-ENHANCING THERAPEUTIC AND USE

BACKGROUND OF THE INVENTION

1. Technical Field

The present invention relates to pharmaceutical compositions for enhancement of libido. The present invention also relates to methods of enhancement of libido in humans and animals.

2. Background Art

Many men and women suffer from a low libido, sexual dysfunction (including erectile dysfunction), or low sexual desire. As men and women age, sexual desire and function can decrease. Other factors can lead to low libido including stress and anxiety, depression, mental disorders, diseases (diabetes), obesity, high blood pressure, high cholesterol, medication side effects (such as from SSRI-type antidepressants or antihypertensives), low testosterone levels (as may be the case in swine and dairy cows), and low dopamine levels in the brain.

There are several different treatments available for low libido or sexual dysfunction. Sildenafil (VIAGRA®, Pfizer) is used to treat erectile dysfunction by inhibiting c-GMP-specific phosphodiesterase type 5 (PDE5) to regulate blood flow. Sildenafil for the treatment of impotence is described in U.S. Pat. No. 6,469,012 to Ellis, et al. Sildenafil must be administered an hour prior to sexual intercourse.

There have been negative side effects of using sildenafil, including sudden hearing loss, headache, flushing, impaired vision, severe hypotension, myocardial infarction, and stroke.

U.S. Pat. No. 4,087,524 to Grunwell, et al. discloses derivatives of androst-4-en-19-ol which are useful in enhancing the libido and related psychic attitudes in primates.

CA 2498267 to Dudley discloses a transdermal hydroalcoholic testosterone gel formulation that overcomes the problems associated with other testosterone delivery mechanisms by providing, among other things, a desirable pharmacokinetic hormone profile with little or no skin irritation. The gel may be used as a method of improving sexual performance, including treating erectile dysfunction, and increasing libido by increasing testosterone levels in men. In addition, the gel may be used in conjunction with pharmaceuticals aimed at treating erectile dysfunction, such as sildenafil (VIAGRA®, Pfizer), to enhance their effectiveness.

U.S. Pat. No. 6,734,186 to Maw, et al. discloses a method of treating a female suffering from FSD (female sexual dysfunction), in particular FSAD. The method comprises delivering to the female an agent that is capable of potentiating cAMP in the sexual genitalia; wherein the agent is in an amount to cause potentiation of cAMP in the sexual genitalia of the female. The agent may be admixed with a pharmaceutically acceptable carrier, diluent or excipient.

U.S. Patent No. 2009/0202662 to Fouche, et al. discloses a process for the production of a substance or composition for the therapeutic or prophylactic treatment of erectile dysfunction or the enhancement of libido in a male human or animal subject that includes the step of formulating the substance or composition from at least one of plant material and an extract of plant material of at least one plant species of the family Geraniaceae.

Cherkasov, et al. (J. Med. Chem. 2005, 48, 3203-3213) describes nonsteroidal ligands for human sex hormone binding globulin. Models were based on 5α-dihydrotestosterone (DHT) and the nonsteroidal ligands had the ability to displace DHT.

Kumar, et al. (Journal of Steroid Biochemistry & Molecular Biology 71 (1999) 213-222) teaches dose response of ventral prostate (VP) and levator ani (LA) to T, dihydrotestosterone (DHT), 19-nortestosterone (19-NT), 7a-methyl-19-NT (MENT), 7a-cyano-19-NT (CNNT), and 7a-acetyl-thio-19-NT (ATNT) in castrated rats. The most potent androgenic steroid (VP response) was MENT followed by T, DHT, 19-NT, ATNT, and CNNT. On the other hand, the order of anabolic potency (LA response) was MENT>19-NT>T>DHT>ATNT>CNNT.

There remains a need for an effective treatment for low libido and sexual enhancement. There further remains a need for new steroid treatments that can affect low libido and sexual enhancement, as well as treatments for breeding synchronization in animals.

SUMMARY OF THE INVENTION

The present invention provides for a composition for enhancing libido of a pharmaceutically effective amount of a libido-enhancing therapeutic of (5S,10R,13S,17S)-13-methyl-3-oxohexadecahydro-1H-cyclopenta[a]phenanthren-17yl acetate (Formula I), (3S,5S,10R,13S,17S)-3-hydroxy-13-methylhexadecahydro-1H-cyclopenta[a]phenanthren-17yl acetate (Formula II), (5S,10S,13S,17S)-17-hydroxy-13-methyltetradecahydro-1H-cyclopenta[a]phenanthren-3(2H)-one (Formula III), a nandrolone derivative lacking a double bond at C4-C5, optionally including an acetate group at C17 or optionally including another chemical group substituted for acetate at C17, isomers thereof, analogs thereof, or combinations thereof, and a pharmaceutically acceptable carrier.

The present invention also provides for a method of enhancing libido, by administering the composition of the present invention to an individual in need of an enhanced libido, and enhancing libido in the individual.

The present invention also provides for a method of enhancing libido, by administering the composition of the present invention to an individual at an age when libido and sexual desire have naturally decreased, and enhancing libido in the individual.

The present invention provides for a composition for enhancing libido and arousal, including a pharmaceutically effective amount of a libido-enhancing therapeutic in combination with a sexual dysfunction therapeutic.

The present invention also provides for a method of enhancing libido and arousal by administering the composition of the present invention in combination with a sexual dysfunction therapeutic to an individual in need of an enhanced libido and arousal, and enhancing libido and arousal in the individual.

DESCRIPTION OF THE DRAWINGS

Other advantages of the present invention are readily appreciated as the same becomes better understood by reference to the following detailed description when considered in connection with the accompanying drawings wherein:

FIG. 5A is a table of ADMET Predicted Profile, Classification and FIG. 5B is a table of ADMET Predicted Profile, Regression for nandrolone;

FIG. 6A is a table of ADMET Predicted Profile, Classification and FIG. 6B is a table of ADMET Predicted Profile, Regression for Formula (I);

FIG. 7A is a table of ADMET Predicted Profile, Classification and FIG. 7B is a table of ADMET Predicted Profile, Regression for Formula (II);

FIG. 8A is a table of ADMET Predicted Profile, Classification and FIG. 8B is a table of ADMET Predicted Profile, Regression for Formula (III);

DETAILED DESCRIPTION OF THE INVENTION

The present invention is generally directed to compositions of libido-enhancing therapeutic and methods of enhancing libido and sexual activity. Most preferably, the composition is a libido-enhancing therapeutic of Formula (I), Formula (II), Formula (III), isomers thereof, analogs thereof, or combinations thereof. Preferably, the composition is a pharmaceutical composition that includes a pharmaceutically effective amount of Formula (I), Formula (II), Formula (III), isomers thereof, analogs thereof, or combinations thereof and a pharmaceutically acceptable carrier. The libido-enhancing therapeutic includes a steroidal poly-ring structure without androgenic or other typical steroidal activities.

Figure 1:
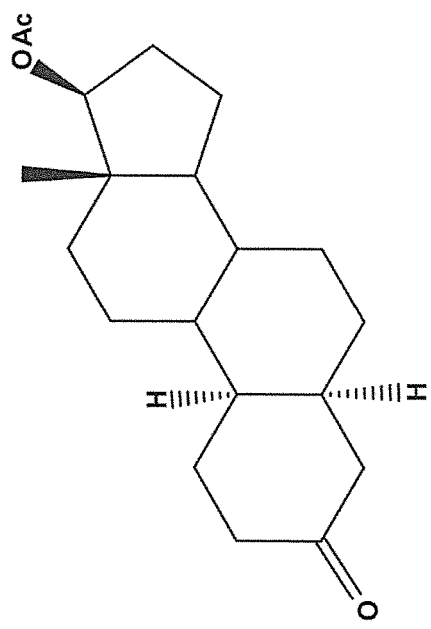
FIG. 1 is a chemical formula and properties of the libido-enhancing therapeutic of Formula (I) of the present invention.

Formula (I) is shown in FIG. 1, and is (5S,10R,13S,17S)-13-methyl-3-oxohexadecahydro-1H-cyclopenta[a]phenanthren-17yl acetate. Formula (I) has the CAS Registry Number 5138-34-1. The bioconcentration factor is 1900, the Koc is 7740, the log D is 4.62, the log P is 4.617+/−0.317, it is sparingly soluble, has a boiling point of 422.7+/−45 degrees C., and a melting point of 112.5 degrees C.

Figure 2:
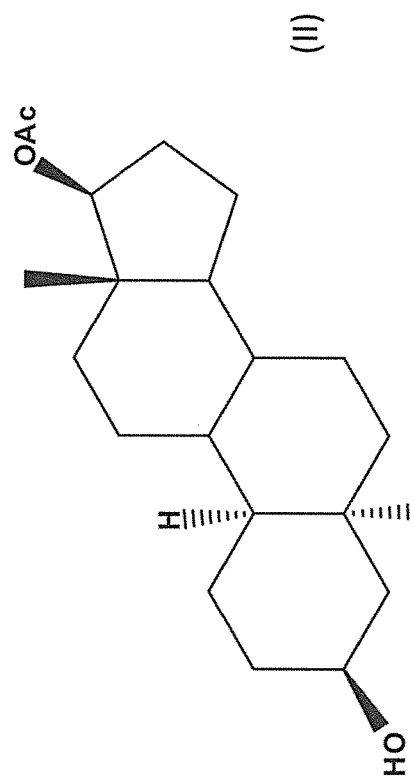
FIG. 2 is a chemical formula and properties of the libido-enhancing therapeutic of Formula (II) of the present invention.

Formula (II) is shown in FIG. 2, and is (3S,5S,10R,13S,17S)-3-hydroxy-13-methylhexadecahydro-1H-cyclopenta[a]phenanthren-17yl acetate. Formula (II) has the CAS Registry Number 889870-64-8. The bioconcentration factor is 4260, the Koc is 13800, the log D is 5.08, the log P is 5.078+/−0.263, it is sparingly soluble, and has a boiling point of 424.6+/−18.0 degrees C.

Figure 3:
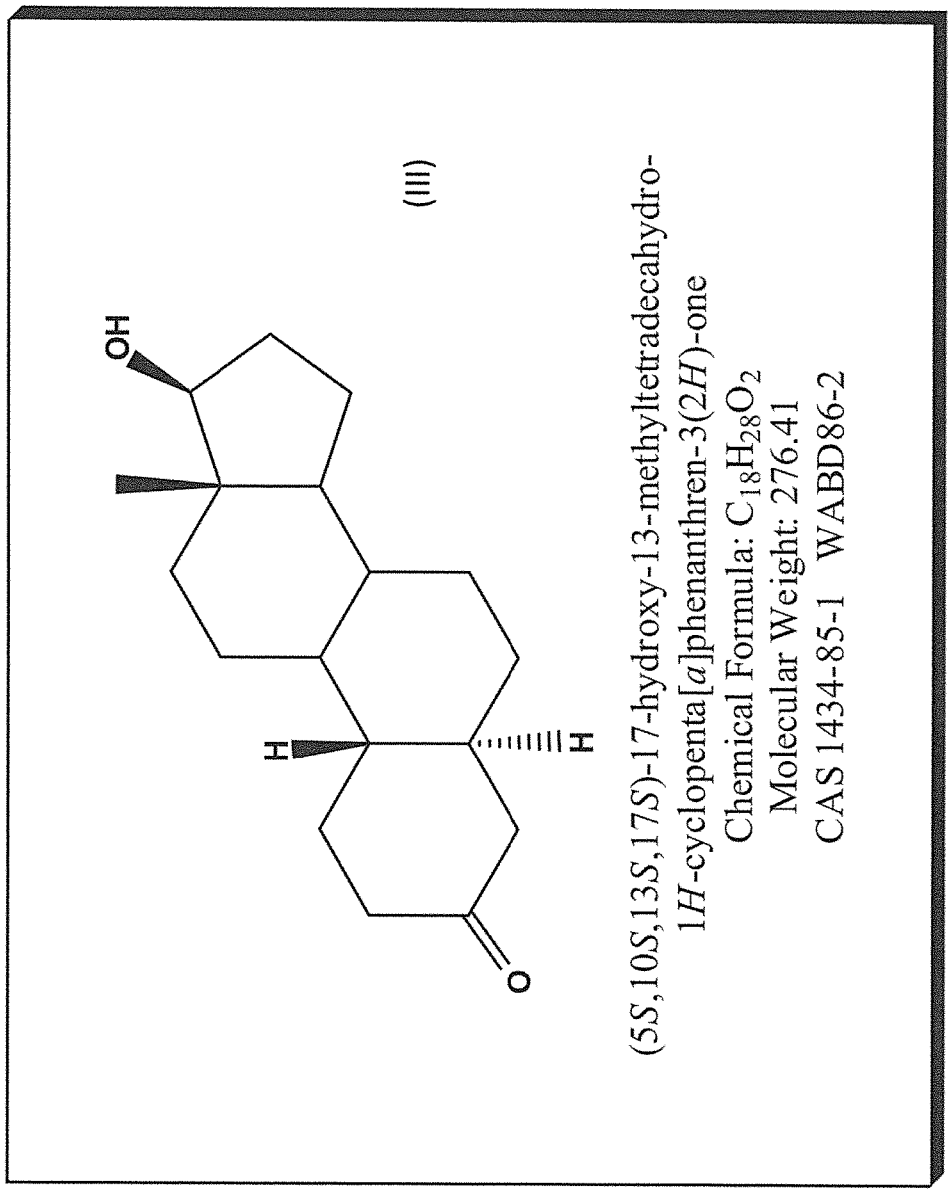
FIG. 3 is a chemical formula and properties of the libido-enhancing therapeutic of Formula (III) of the present invention.

Formula (III) is shown in FIG. 3, and is (5S,10S,13S,17S)-17-hydroxy-13-methyltetradecahydro-1H-cyclopenta[a]phenanthren-3(2H)-one. Formula (III) has the CAS Registry Number 1434-85-1. The bioconcentration factor is 351, the Koc is 2310, the log D is 3.65, the log P is 3.651+/−0.300, it is sparingly soluble, has a boiling point of 412.9+/−45.0 degrees C., and a melting point of 130-134 degrees C. depending on the solvent.

The compositions of the present invention are steroids; however, the compositions only share a steroid skeleton of nandrolone and do not have all of the same structural characteristics but share some such as the estrene backbone. Nandrolone is 19-nor testosterone. Nandrolone in the decanoate ester form is used in osteoporosis treatment, aplastic anemias, and even some neoplasias. Nandrolone is not broken down into DHT (dihydroxytestosterone), but rather a much weaker androgen dihydroandrolone (DHN or Formula III) (by the 5 alpha reductase enzyme), which is much less antagonistic of the sex hormone receptor than other androgens. Therefore, nandrolone does not have the harmful side effects on the scalp, skin, and prostate that other anabolic steroids like testosterone do because these tissues have high levels of 5 alpha reductase enzyme which converts nandrolone to DHN which has less anabolic activity. The 5 alpha reductase enzyme converts testosterone to DHT which has more anabolic activity than testosterone and therefore testosterone affects the prostate much more than nandrolone. Also, the lack of alkylation of the 17α-carbon on nandrolone greatly reduces its liver toxicity. There are side effects of nandrolone, however, including reduced libido (due to testosterone suppression), erectile function, water retention, gynecomastia, natural testosterone suppression, high blood pressure, and high cholesterol. The compositions of the present invention have greatly reduced or eliminated side effects compared to other steroids because all of the compounds in the invention have been essentially 5 alpha reduced by loss of the double bond and share a similar structure to DHN or is DHN (Formula III). One compound (Formula II) is structurally similar to the metabolite of DHN. Formula II is the metabolite of DHN when DHN is enzymatically modified by 3 alpha hydroxyl dehydrogenase. Formula II also has an acetate group at C17 that DHN does not.

The present invention also provides for compositions that are nandrolone derivatives lacking a double bond at C4-C5, optionally including an acetate group at C17 or optionally including another chemical group substituted for acetate at C17.

The compositions are in the structural class of estrene steroids. The compositions of Formulas (I), (II), and (III) have unnatural optical stereoisomers. The compositions can be a testosterone mimic.

The composition can be administered in a tablet form, capsule form, topical application form, food or drink additive, or any other suitable form. The composition can be formulated for immediate release, extended release, or delayed release depending on the release profile desired. Various coatings, excipients, or prodrugs can be used to accomplish the desired release profile. The composition can be administered once a day, multiple times a day, multiple days, or at other suitable times such as at a time prior to sexual activity. The composition can be dosed at 0.05 mg to 1000 mg per day.

The composition is preferably used to enhance sexual desire and libido. Sexual desire is controlled by brain systems involved in sexual excitation and inhibition, which include the hypothalamus and amygdala. Neurotransmitters such as dopamine in these regions of the brain send signals to control this sexual desire but the neurotransmitters are controlled by receptors in the brain such as the androgen receptor and estrogen receptor. Thus, testosterone and testosterone-like chemicals are involved in controlling sexual desire. Brain dopamine systems (incertohypothalamic and mesolimbic) that link the hypothalamus and the limbic system appear to form the core of the excitatory system, i.e., libido enhancement. This system also includes melanocortins, oxytocin, and norepinephrine. Brain opioid, endocannabinoid, and serotonin systems are activated during periods of sexual inhibition, and blunt the ability of excitatory systems to be activated. Drugs that stimulate the activation of the hypothalamic dopamine or that blunt endocannabinoid or serotonin release and/or postsynaptic binding can be effective in stimulating sexual desire in animals and humans (J Sex Med 2009).

Arousal disorders are distinct from desire disorders with the former involving blood flow to genitals and can be treated with drugs like Viagra while the latter is a "psychological" sexual interest or desire and can be treated with testosterone. Testosterone is important for a number of functions in human development and binds to several receptors including the androgen receptor in a number of different tissues. These androgenic effects of testosterone include testes formation, spermatogenesis, muscle mass, fat deposition, and sexual desire to name a few. Testosterone binds to receptors such as the androgen receptor and can be metabolized in different tissues into more activate (or less active) molecules.

There are many different androgenic chemicals in the body with most sharing the C19 structure, although all do not have to have this structure. For instance, some C-18 steroid derivatives can have more androgenic activity than testosterone in some bioassays. Structural modifications of testosterone or testosterone like chemicals can lead to increase activity in given tissues. Testosterone can be 5-alpha reduced to DHT by prostatic tissue leading to increased androgenic activity while alpha reduction of 19-nortestosterone (nandrolone) to DHN does not increase activity because DHT has increased anabolic activity while DHN has decreased anabolic activity. Thus, different structural modifications can have different effects on different structures and may change potency of steroid derivatives to their receptors. These changes can lead to different effect dose ranges of steroids that need to be administered to observe an androgenic effect. The doses of steroids can range from 0.05 mg to 1,000 mg depending on structure and route of administration.

Receptor binding can be different in different tissues. Most tissues in mice have been shown to have androgen and estradiol receptors. Binding to the androgen receptor occurs at different times after testosterone administration in different tissues and binding can also be altered by the presence of other steroidal agents.

As humans age, particularly males, testosterone levels decrease and androgen effects decrease. The loss of testosterone affects all organs, including the brain, which leads to a lower libido. Testosterone replacement has been recently approved by the FDA for males to counter the symptoms of low testosterone seen with aging. Although this treatment can be effective and can increase libido, it often takes several months before the effects are observed and there are other undesirable androgenic effects associated with testosterone.

The present invention does several things to increase the libido and focuses on the increase in libido as opposed to all the androgenic effects provided by testosterone because derivatives of nandrolone which are 5 alpha reduced and thus have less anabolic activity are used (Formulas I, II, and III). First, a more potent effect on the brain can lead to a higher libido. Second, a more potent effect can allow for an increase of libido in hours, days, or weeks rather than months. If use of the composition of the present invention is stopped, this can lead to a normalization or return of the libido to base line (i.e. the level before the composition was administered). Therefore, the present invention can be used for libido enhancement on a shorter-term basis than the months needed for testosterone. Third, the composition of the present invention can be used on an intermittent basis since its affects can be observed quicker than testosterone, and thus some of the negative androgenic side effects of long term testosterone use can be avoided while still obtaining the libido enhancing benefits of the invention. Fourth, the present invention can have fewer side effects, due to structural differences, than other steroids or related compounds, such as testosterone, administered and used for libido enhancement. Any one of these four outcomes is an improvement over current testosterone replacement therapy.

Therefore, the present invention provides for a method of enhancing libido, by administering the composition of the present invention to an individual in need of an enhanced libido, and enhancing libido in the individual. The compositions increase libido and sexual desire and performance in the individual.

The compositions can be administered to individuals including men and women human subjects, and male and female animals. The composition can be used to treat any man or woman who has a decreased libido or sexual desire in order to enhance libido and return it to normal levels and allow the individual to desire sexual activity. The composition can be used to treat an individual who has decreased libido due to many factors including, but not limited to, stress, illness, pregnancy, weight loss, malnourishment, anemia, smoking, alcohol use, drug use, or medication side effects. Any male or female animal can also be treated, such as, but not limited to, dog, cats, birds, horses, swine, dairy and beef cattle, llamas, goats, other forms of livestock, alpacas, deer, bison, other forms of domesticated and native ruminants, other primates, large felines, bears, rhinoceroses, or any other animal. With animal administration, breeding and reproduction programs can be aided by stimulating reproduction in the animals, especially when it is difficult to get male and female animals to engage in sexual intercourse, or to get females to stand for mounting or artificial insemination. Such use can aid older animals in reproduction, animals that have been ill, or animals with endangered or critically endangered status in repopulation programs. The libido enhancement can also be useful when particular genetics are desired in offspring, such as for show animals and racehorses.

The compositions can be administered over short term (days or weeks) or long term (months or years). The compositions can also reduce fatigue during sexual intercourse as well as sustain the individual's libido for a period of time (such as greater than seven hours) as evidenced in EXAMPLE 2 below.

The compositions can be administered to individuals at an age when libido and sexual desire have naturally decreased, such as 40 years and above, 50 years and above, and 60 years and above in humans. Therefore, the present invention also provides for a method of enhancing libido, by administering the composition of the present invention to an individual at an age when libido and sexual desire have naturally decreased, and enhancing libido in the individual. Due to some disease states, this can also occur at younger ages too.

As described above, the libido-enhancing therapeutic compositions have the ability to generate and increase sexual desire, but they do not have the ability to enhance arousal, physical sexual function, or performance. Therefore, the compositions can also be administered in combination with other sexual dysfunction therapeutics for arousal issues, such as, but not limited to, sildenafil (VIAGRA®, Pfizer), tadalafil (CIALIS®, Lilly USA), vardenafil (LEVITRA®, Bayer AG), avanafil (STENDRA®, Vivus, Inc.), bremelanotide, or alprostadil. The sexual dysfunction therapeutics can be used to treat any type of arousal issues such as erectile dysfunction or female sexual dysfunction. Dosage can be as follows: sildenafil—25 mg to 100 mg once daily, tadalafil—2.5 mg to 20 mg once daily, vardenafil—5 mg to 20 mg once daily, avanafil—50 mg to 200 mg once daily, alprostadil—0.2 to 140 mcg per day. The libido-enhancing therapeutic can be delivered at the same time as the sexual dysfunction therapeutic, or at different times. The libido-enhancing therapeutic can be contained within its own dosage form, within the dosage form together with the sexual dysfunction therapeutic (i.e. a capsule containing the libido-enhancing therapeutic and the sexual dysfunction therapeutic), or within the dosage form itself (i.e. a capsule coating that includes the libido-enhancing therapeutic, with the sexual dysfunction therapeutic within the capsule). The composition of the present invention can be tailored to provide different release profiles as needed or desired for a particular individual, such as, but not limited to, sustained release, prolonged release, or immediate release. The libido-enhancing therapeutic and the sexual dysfunction therapeutic can each have the same release profiles or different release profiles. Therefore, the present invention provides for a composition for enhancing libido and arousal, including a pharmaceutically effective amount of a libido-enhancing therapeutic in combination with a sexual dysfunction therapeutic.

The present invention also provides for a method of enhancing libido and arousal by administering the composition of the present invention in combination with a sexual dysfunction therapeutic to an individual in need of an enhanced libido and arousal, and enhancing libido and arousal in the individual. Any of the libido-enhancing therapeutics and sexual dysfunction therapeutics as described above can be used.

The compound of the present invention is administered and dosed in accordance with good medical practice, taking into account the clinical condition of the individual patient, the site and method of administration, scheduling of administration, patient age, sex, body weight and other factors known to medical practitioners. The individual is preferably human, but can also be an animal. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. Topical application with absorption through the skin can be a good means of delivery. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days to several months. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

A male human came in physical contact with the compositions of the libido-enhancing therapeutics of Formula (I), Formula (II), and Formula (III) by accident while synthesizing the compositions. He experienced a weekend-long period of arousal and increased libido.

Example 2

In Silico Analysis and Libido Stimulation Evaluations in Rats Treated with Nandrolone Congeners Methodology Drugs.

Drugs used in these evaluations were nandrolone and three nadrolone congeners. All the congeners lacked the double bond structure of nandrolone. Two had an acetate group in C17. This group could stabilize the congener, make it more readily absorbed into the body, or affect the metabolism such that a metabolite of the congener is the libido-enhancing chemical. There are other possibly explanations as to why the acetate group at C17 may be important.

Figure 9:
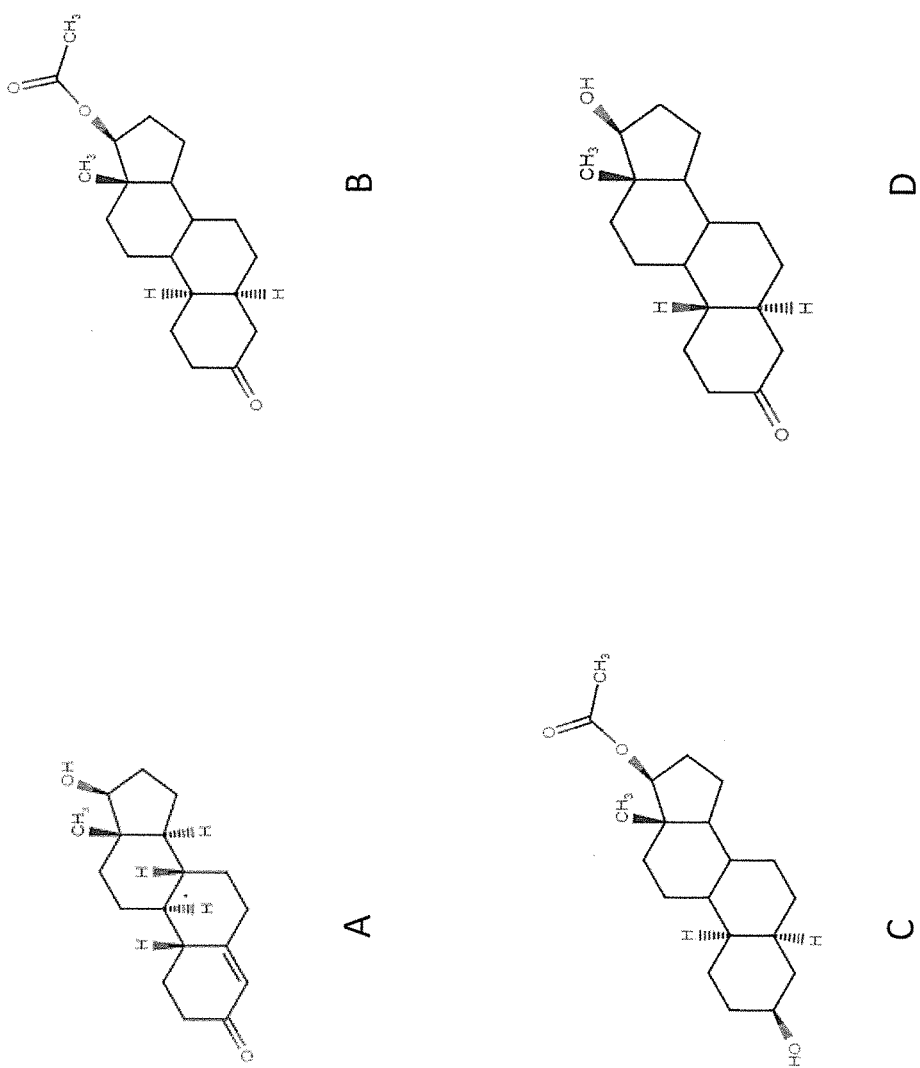
FIG. 9A is a representation of nandrolone.
FIG. 9B is a representation of Formula (I)
FIG. 9C is a representation of Formula (II)
FIG. 9D is a representation of Formula (III)

The structures are shown in FIGS. 9A-9D. FIG. 9A is the structure of nandrolone. FIG. 9B is congener 1 (D1) (Formula I). FIG. 9C is congener 2 (D2) (Formula II), and FIG. 9D is congener 3 (D3) (Formula III).

In Silico Evaluations.

In silico theoretical evaluations were carried out as proposed by Pinheiro, et al. (2012) and different descriptors were selected for analysis as described below. These parameters that take into account hydrophobic profile, related to oral bioavailability, and electronic properties of substances may be used to generate a range of values/points that classify the molecule as a potential drug that could be used clinically.

Descriptor were analyzed using the methods of OSIRIS Property Explorer, MedChem Designer (Simulations Plus, Inc.), and MarvinSketch (ChemAxon, admetSAR, and FAFDrugs2 as shown in TABLE 1. All methods used are free software available on the World Wide Web (Internet).

TABLE 1

Descriptors select for in silico analysis

| Physic-chemical | ADMET |
|---|---|
| CLogP | Environmental Toxicity |
| Log S | AMES test |
| Molecular Weight | Oral Bioavailability and Absorption |
| # Hydrogen Bonds Donors | CYP450 Inhibitor/Substrate |
| # Hydrogen Bonds Acceptors | Lethal Dose |

In Vivo Studies

Animals.

Female and male rats (*Rattus novergicus*) Wistar strain, with 200-280 g and 8-12 weeks old, were purchased from University of São Paulo Central Animal Care Unity. They were kept in controlled environment, including dark-light periods (12 hours each), temperature (22° to 25° C.), and with free access to water and food.

Ovariotomy.

Female Wistar rats, weighing about 250 g, were ovariectomized. The procedure initiated inducing general anesthesia with Dopalen (Ketamin 70 mg/kg) and Anasedan (Xilazin 12 mg/kg), then abdominal wall was sutured by the linea alba region, ovaries location, ligation of vessels supplying the ovaries and the procedure was completed with ovariectomy, itself, as well as the suture of the abdominal wall and skin. After surgery the animals received analgesic (tramadol 2 mg/kg), antibiotic (enrofloxacin, 10 mg/kg) and anti-inflammatory (Maxicam—2 mg/kg) for at least one week, or more if necessary.

Pseudo-estrus inducing. The females received estradiol (0.2 mg/day) subcutaneously for two weeks after ovariotomoy for pseudo-estrus state inducing. This condition was evaluated by vaginal smears each two days after estradiol treatment beginning. Sterile cotton-tipped swabs wetted in distilled water were gently and quickly introduced into the vaginal orifice, carefully rotated (one twist) against the vaginal wall. Rats were not anesthetized during smear collection. Afterwards, the collected sample of vaginal epithelial cells was placed on glass slides, dried at 37° C., and fixed in an ethanol-ether solution (1:1) for one minute.

The slides were then examined under light microscopy. Only females in pseudo-estrus conditions were used for libido stimulation assessment (PACCOLA et al, 2013).

Libido stimulation assessment. For libido stimulation assessments, first male rats, weighing about 250-280 g, had their penis anesthetized with 2% lidocaine by topical route 10 minutes before treatment. The three drugs were administered orally at 50 mg/kg each two days for six days (each rat received three doses). Nandrolone (IM) was used as the positive control group while olive oil and water were used as negative controls (orally administrated), as described below in TABLE 2. After one hour of treatment, couples were put together in a box, and a video camera with night vision was adequately positioned to encompass all the groups in the video, recording overnight the matches.

TABLE 2

Groups for Libido Stimulation Assessment

| GROUP | ROUTE | # ANIMALS |
|---|---|---|
| NEGATIVE CONTROL (WATER) | ORAL | 4 |
| SOLVENT CONTROL (OLIVE OIL) | ORAL | 4 |
| 5138-34-7 | ORAL | 4 |
| 889870-64-8 | ORAL | 4 |
| 1434-85-1 | ORAL | 4 |
| NANDROLONE | INTRAMUSCULAR | 4 |

Analysis of the videos was performed according to the following parameters: time to first mating, duration of mounts, and quantity of mounts.

Results.

In silico tools are computational tools that use different types of software that enabled advances in predicting in vivo performance of drugs, changing the way drugs are developed and revised. The modeling and simulation methods are now widely used in the study of products and regulatory review of drugs. Parameters that take into account hydrophobic profile, related to oral bioavailability, and electronic properties of substances may be used to generate a range of values/points that classify the molecule as a potential drug that could be used clinically.

The software OSIRIS Property Explorer, widely used software to evaluate Druglikeness and Drug-Score. This software enables the forecasting of whether a molecule has the potential to act as drug (Drug-Likeness) based on topological descriptors, key structural markers and/or other properties such as Clog P (partition coefficient octanol/water) and molecular weights. In this program, the occurrence of each fragment is determined among a collection of commercial drugs and a collection of alleged "non-drug" compounds Fluka. In the same manner, Drug-Score is the combination values of Drug-Likeness, Clog P, log S, molecular weight and toxicological hazards. This value is often used for the assessment and determination of the best molecules in a series of compounds, and thus serves as a decision to select the best compounds based on Drug-Score for the continuation of evaluations in in vitro and in vivo studies.

The softwares MedChem Designer (Simulations Plus, Inc) and MarvinSketch (ChemAxon) are used to evaluate if molecules can demonstrate the physicochemical parameters and the Lipinski "Rule of 5" of a potential drug. This rule lists the requirements for a hydrophobic molecule to be well absorbed orally and is based on the distribution of the calculated properties among some thousands of different drugs available in libraries. According to the authors' proposal, a molecule with a good potential to be well absorbed orally requires: (a) molecular weight less than 500 Da; (b) log P below 5; (c) having less than 5 connections donor H (+); (d) have less than 10 links acceptors for H(+).

Figure 4A:
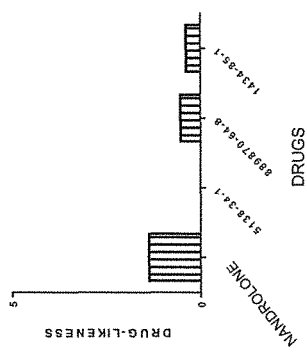
FIG. 4A is a graph of Drug-Likeness.
Figure 4B:
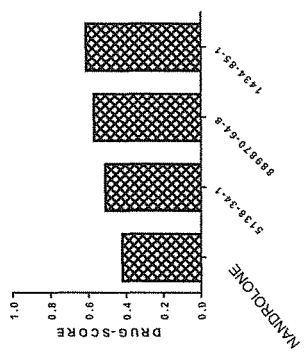
FIG. 4B is a graph of Drug-Score.

Formulas (I), (II) and (Ill), were compared according to the potential drug calculation of a molecule (Druglikeness), based on its electronic properties and hydrophobicity values (FIG. 4A) and also by the Drug-score, a parameter that combines the Druglikeness, cLog P, molecular weight and potential toxic risks (FIG. 4B) using Osiris software. Although nandrolone showed the best Druglikeness values which, in theory, would make it seem like a good molecule to become a drug, it presented the worst Drug-score, due to the combination of the other important parameters listed below. The Formulas (I), (II), and (III) exhibited low Drug-likeness values, especially when compared with nandrolone; however, they showed good Drug-scores, showing they are good candidates to become a drug/medicine.

It is important to note that based on review of the literature, this is the first time that these parameters have been evaluated for Formulas (I), (II), and (III). However, this evaluation makes sense since all the formulas are or are associated with metabolism of nandrolone. Nanadrolone has been shown in the experiments to enhance libido early (hours) on but in clinical practice Nandrolone actually decreases libido over time (days to weeks) because it decreases testosterone. Nandrolone initially undergoes metabolism by 5 alpha reductase enzyme to dihydroxynandrolone (DHN). Nandrolone (FIG. 9A) is known to have reduced anabolic effects when it is metabolized. FIG. 9D is DHN, FIG. 9B is DHN with the acetyl group. FIG. 9C is the metabolite of DHN with an acetyl group. Therefore, these compounds should all have less anabolic side effects than nandrolone. When developing a drug for libido enhancement it is important that the drug has low toxicity, low anabolic activity but high libido enhancing effects.

Figure 4C:
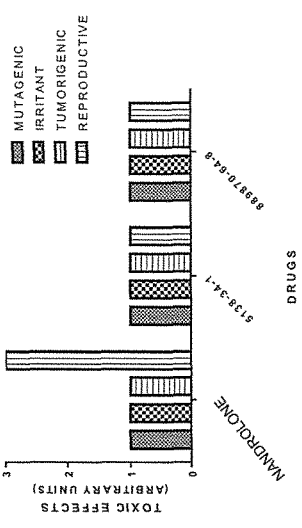
FIG. 4C is a graph of Toxic Effects for nandrolone, and Formulas (I), (II), and (III)

The potential toxic risks of the novel drugs were compared with nandrolone risks and were calculated by Osiris software (FIG. 4C). This analysis indicates that Formulas (I), (II), and (III) presented low to non-potential toxic risks for clinical use, different than nandrolone which showed high potential reproductive toxicity. ADMET information is shown for nandrolone (FIGS. 5A and 5B), Formula (I) (FIGS. 6A and 6B), Formula (II) (FIGS. 7A and 7B), and Formula (III) (FIGS. 8A and 8B). A summary of the ADMET information is shown in TABLE 3.

TABLE 3

Comparative ADMET profile evaluation of Nandrolone, 5138-34-1, 889870-64-8 and 1434-85-1. All evaluations were carried out using the AdmetSar software (CHENG et al., 2012).

| EVALUATION | NANDROLONE RESULT | 5138-34-1 RESULT | 889870-64-8 RESULT | 1434-85-1 RESULT |
|---|---|---|---|---|
| ABSORPTION | | | | |
| Blood Brain Barrier | Highly Permeable | Highly Permeable | Highly Permeable | Highly Permeable |
| Human Intestinal | Highly Permeable | Highly Permeable | Highly Permeable | Highly Permeable |
| CACO-2 Permeability | Permeable | Permeable | Permeable | Permeable |
| Renal Organic Cation Transporter | Non-Inhibitor | Non-Inhibitor | Non-Inhibitor | Non-Inhibitor |
| DISTRIBUTION METABOLISM | ND | ND | ND | ND |
| CYP450 2C9 Substrate | Non-substrate | Non-substrate | Non-substrate | Non-substrate |
| CYP450 2D6 Substrate | Non-substrate | Non-substrate | Non-substrate | Non-substrate |
| CYP450 3A4 Substrate | Substrate | Substrate | Substrate | Substrate |
| CYP450 1A2 Inhibitor | Non- Inhibitor | Non- Inhibitor | Non- Inhibitor | Non- Inhibitor |
| CYP450 2C9 Inhibitor | Non- Inhibitor | Non- Inhibitor | Non- Inhibitor | Non- Inhibitor |
| CYP450 2D6 Inhibitor | Non- Inhibitor | Non- Inhibitor | Non- Inhibitor | Non- Inhibitor |
| CYP450 2C19 Inhibitor | inhibitor | Non- Inhibitor | Non- Inhibitor | Non- Inhibitor |
| CYP450 3A4 Inhibitor | Non- Inhibitor | Non- Inhibitor | Non- Inhibitor | Non- Inhibitor |

TABLE 3-continued

Comparative ADMET profile evaluation of Nandrolone, 5138-34-1, 889870-64-8 and 1434-85-1. All evaluations were carried out using the AdmetSar software (CHENG et al., 2012).

| EVALUATION | NANDROLONE RESULT | 5138-34-1 RESULT | 889870-64-8 RESULT | 1434-85-1 RESULT |
|---|---|---|---|---|
| EXCRETION TOXICITY | ND | ND | ND | |
| Human Ether-a-go-go-Related Gene Inhibition (hERG) | Weak | Weak | Weak | Weak |
| AMES Toxicity | Negative | Negative | Negative | Negative |
| Carcinogens | Negative | Negative | Negative | Negative |
| Fish Toxicity | High | High | High | High |
| Tetrahymena pyriformis Toxicity | High | High | High | High |
| Honey Bee Toxicity | High | High | High | High |
| Biodegradation | Not ready biodegradable | Not ready biodegradable | Not ready biodegradable | Not ready biodegradable |
| $LD_{50}$ Acute Toxicity - Rats | 1.6594 mol/Kg | 1.6933 mol/Kg | 2.0714 mol/Kg | 1.9534_mol/Kg |

Noteworthy from TABLE 3 is that all compounds exhibit very similar profile, what is expected considering the chemical similarities. The most remarkable difference is in Rat $LD_{50}$ of compound 889870-64-8 higher than others. On the other hand, all compounds showed good oral bioavailability (although nowadays Nandrolone is used as IM drug) with good intestinal absorption and excellent brain barrier permeability. Also, the analysis shows all compounds are metabolized in liver at CYP450 complex.

Using the Marvin software some electronic properties of all molecules were determined. Moreover, the four drugs were also evaluated against the "Rule of 5" proposed by Lipinski, et al. The results are shown in TABLE 4. All drugs met the "Rule of 5" in all parameters.

TABLE 4

Physico-chemical properties and Lipinski "Rule of 5" of Nandrolone, CAS 5138-34-1, CAS 889870-64-8 and CAS 1434-85-1

| | "RULE OF 5" LIPINSKI (2001) | | | | |
|---|---|---|---|---|---|
| DRUG | CLogP | LogD* | HBA | HBD | MW |
| Nandrolone | 3.30 | 3.55 | 2 | 1 | 274.4 |
| (I) 5138-34-1 | 3.69 | 3.34 | 2 | 1 | 318.4 |
| (II) 889870-64-8 | 3.53 | 3.11 | 2 | 1 | 320.5 |
| (III) 1434-85-1 | 3.20 | 3.07 | 2 | 1 | 276.4 |

In summary, In silico evaluations shows high toxicity for nandrolone, at least for the reproductive system. Formulas (I), (II), and (III) displayed similar Drug-score and fit Lipinski's Rule of 5. Formula (III) is a functional isomer of nandrolone; however, it does not show the same potential toxicity. The main difference could be observed at C-4 and C-5 (double bond at nandrolone, absent at the CAS 1434-85-1). Formula (I) and Formula (II) are also functional isomers and also have the C4-C5 double bond missing but have low toxicity, possibly the first having a ketone moiety at C-3 and the latter an alcohol at the same carbon. Also Formula I and Formula II lack the double bond at carbon C-4 and C-5. The metabolism of nandrolone in humans has been shown that the double bond at C4-C5 is removed by the 5 alpha reductase enzyme.

In Vivo Libido Stimulation Assessment

The libido studies focused the investigation in how drugs would stimulate male rats to increase matching. Considering that sexual activity in animals is related with reproduction and not only with pleasure, assessment of increase desire is particular subjective. To ensure that the observations were related with Central Nervous System modulation, 2% Lidocaine was topically applied at penis glans, to avoid any local stimulation.

The animals were treated each two days with 50 mg/Kg of test drugs (given orally), water and olive oil as negative control (given orally) and nandrolone (IM).

Figure 10:
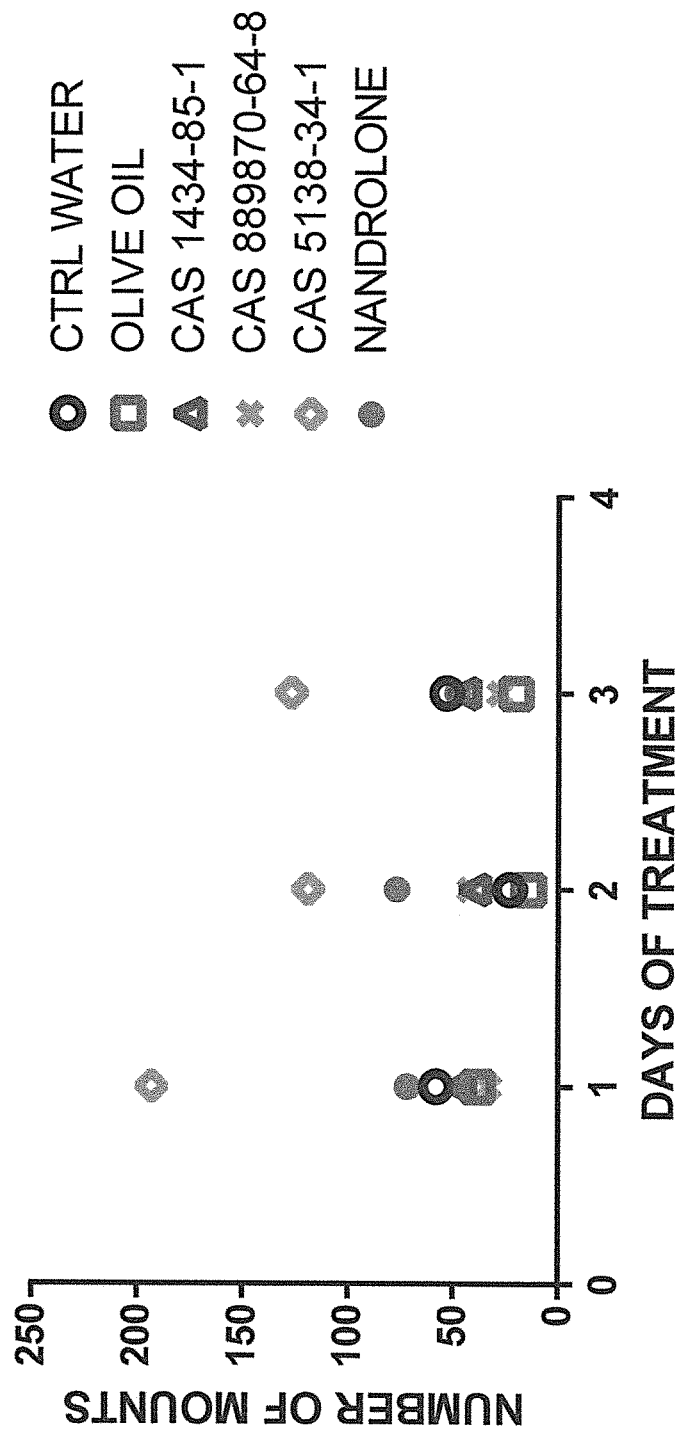
FIG. 10 is a graph of the total number of mounts for couples after each day's treatment.

FIG. 10 shows the total number of mountings after each treatment. The results express mean±SE of two experiments. It is very clear to observe that drug CAS 5138-34-1 (D1) (Formula I) significantly increased the number of mounts, compared with controls and other drugs. A decrease in number of mounts was observed in second and third day treatment. This could be due female conditions, such as the reduced number of females and pre-experimental conditions like ovariotomy and pseudo-estrus induction. It can also be due to simple physical exhaustion of either the male or female or both.

Figure 11:
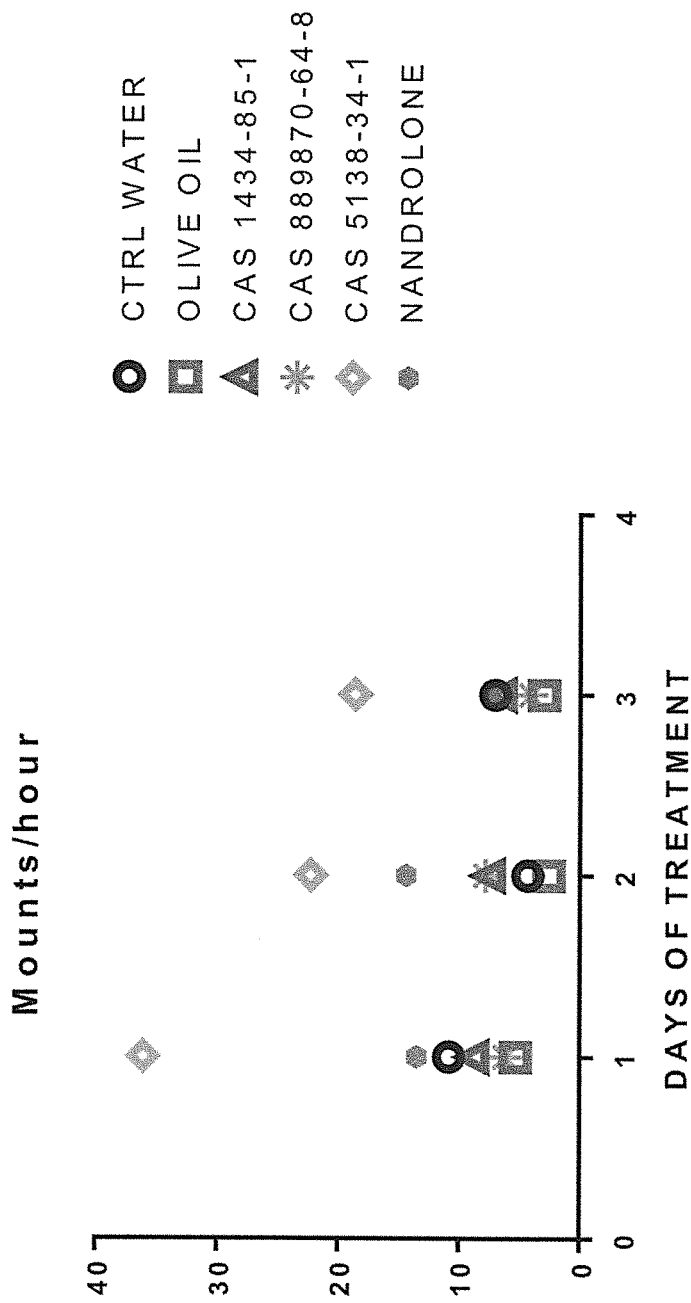
FIG. 11 is a graph of the number of mounts per hour analyzed for couples after each day's treatment.

FIG. 11 shows the number of mounts per hour and the same profile of FIG. 10 is observed. The results express mean±SE of two experiments. The difference between CAS 5138-34-1 (D1) (Formula I) and nandrolone is more than twice. This compound (Formula I) can be more active because of the addition of the acetate group at position C17. This can stabilize the compound and lead to better absorption and distribution in the body. Or, this can lead to a different metabolite profile and it is the metabolite that causes the libido enhancing effects. Thus, chemical modification of Formula I, II, III can enhance their libido enhancing effects. Other modifications to this compound (Formula I) at the same position C17 or different positions can also enhance the effects of this compound (Formula I) or the other compounds (Formula II, III). Most steroid drugs are metabolized by the liver but there are other pathways and tissues for metabolism. Metabolism and binding to plasma proteins like sex hormone binding globulin (SHBG) can affect rate of metabolism, distribution, or onset of the libido enhancing effect.

Figure 12:
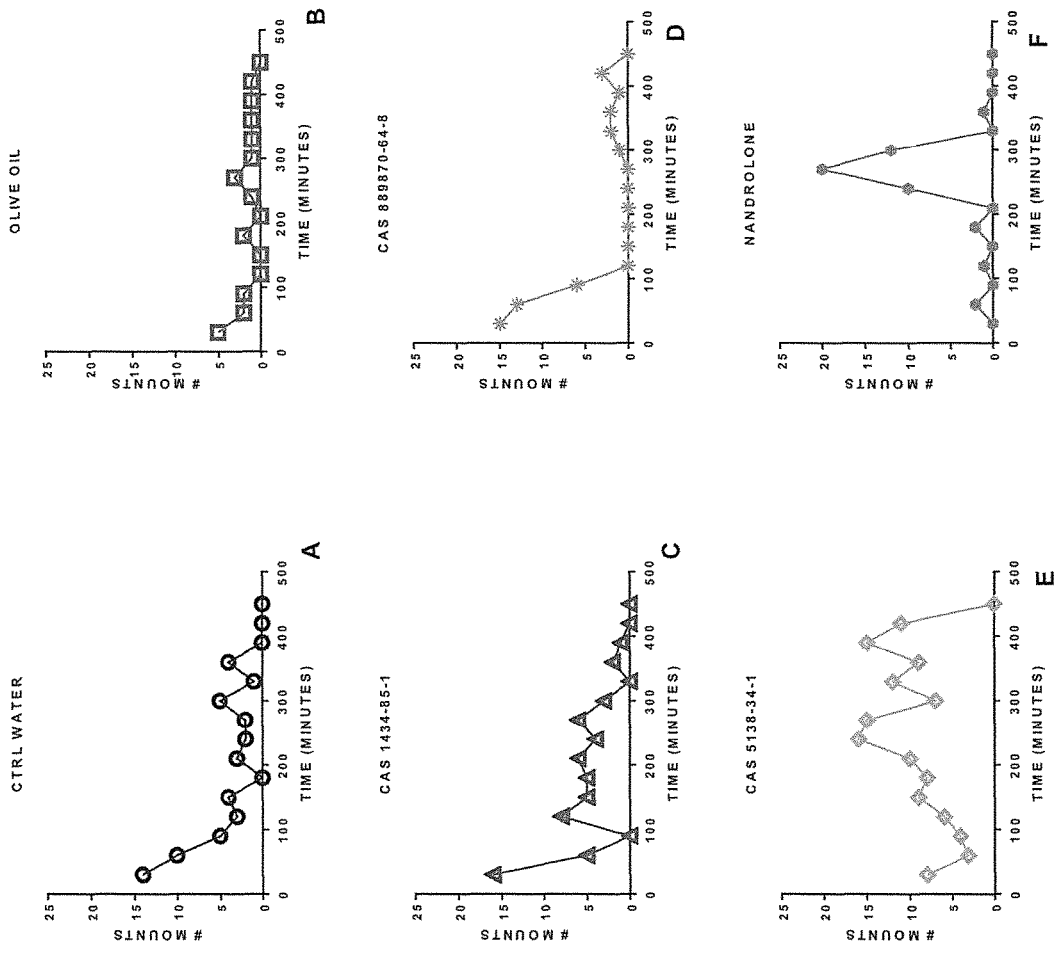
FIGS. 12A-12F are graphs for the total number of mounts for couples of treatment along the night.

Mount kinetics profiles are observed in FIGS. 12A-12F. Each point in the x-axis (time) corresponds to 30 minutes. The results express mean±SE of one experiment. As observed in FIGS. 12A, 12C, and 12D, the animals had great activity just after coupling and ceased no more than 2 hours after. CAS 1434-85-1 (D3) (Formula III) showed few mounts in subsequently hours whereas CAS 889870-64-8 (D2) (Formula II) showed a total decrease of activity after 2 hours coupling. Despite its great activity, CAS 5138-34-1 (Formula I) exhibited low activity at the first three hours after coupling (FIG. 12E). However, an intense and sustainable activity was achieved after the third hour until the seventieth hour of observation. This kind of observation is very important considering the fatigue experienced after sexual intercourse. In case of animals treated with the drug CAS 5138-34-1, no kind of stress of fatigue was observed after each intercourse.

Although in silico observations suggest a promptly oral absorption and blood-brain barrier great permeability, differently of other drugs studied, CAS 5238-34-1 took a long time to have some effect, what could be due an "first passage effect" or liver metabolism, but also, the long time effect could be due to a long half-life time.

Nandrole (FIG. 12F) exhibited low stimulation at the first three hours with a peak of activity at the fourth hour retuning to baseline (zero activity) at the sixth hour. This high activity only after four hours could be due a metabolite activity such as CAS 1434-85-1. There are no PK (blood levels of Formula I, II, III) or metabolite studies on the rat blood in relationship to the mount frequency over time. Therefore, depending on the half life of Formula I, II, III, the chemical causing the increase in mount frequency could be the Formula I, II, III in the blood system of the rat or could be due to metabolism of Formula I, II, III by the rat liver or other organs to give a metabolite that is responsible for the increase mount frequency.

CONCLUSIONS

In silico evaluations show high toxicity for Nandrolone, at least for reproductive system. All novel drugs displayed similar Drug-score and fit Lipinski's Rule of 5. CAS 1434-85-1 (Formula III) is a functional isomer of Nandrolone; however, it does not show the same potential toxicity. The main difference could be observed at C-4 and C-5 (double bond at Nandrolone, absent at the CAS 1434-85-1, CAS 5138-34-1, and CAS 889870-64-8). CAS 5138-34-1 (Formula I) and CAS 889870-64-8 (Formula II) are also functional isomers, having the first a ketone moiety at C-3 and the last one has an alcohol at the same carbon. Formula i and Formula II also have an acetate group at C17. All congeners show similar ADMET profile and high theoretical $LD_{50}$, which indicate safety for further tests. CAS 5138-34-1 exhibits an effective and sustainable late libido stimulation for greater than seven hours. The other drugs showed effects similar to controls.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Jiang W, Kim S, Zhang X, Lionberger R A, Davit B M, Conner D P, Y u LX. 2011 The role of predictive biopharmaceutical modeling and simulation in drug development and regulatory evaluation. Int J Pharm. 418(2):151-160. doi: 10.1016/j.ijpharm.2011.07.024.
2. Valerio L G Jr. 2011. In silico toxicology models and databases as FDA Critical Path Initiative toolkits.Hum Genomics. 5(3):200-207.
3. Dias L R, Santos M B, Albuquerque S d, Castro H C, de Souza A M, Freitas A C, DiVaio M A, Cabral L M, Rodrigues C R. 2007. Synthesis, in vitro evaluation, and SAR studies of potential antichagasic 1H-pyrazolo[3,4-b]pyridine series. Bioorg Med Chem. 15(1):211-219
4. Devereux M, Popelier P L. 2010 In silico techniques for the identification of bioisosteric replacements for drug design. Curr Top Med Chem. 10(6):657-668.
5. Lipinski C A, Lombardo F, Dominy B W, Feeney P J. 2001. Experimental and computational approaches to estimate solubility and permeability in drug discovery and development settings. Advan. Drug Delivery Reviews. 46:3-26.
6. Pinheiro L C S. Rodrigues C R, Ferreira V F, Castro H C, Cabral L M, Saulo B, Bernadino A, Magãlhaes U O, Oliveira D S. 2012. Searching for new antileishmanial lead drug candidates: Synthesis, biological and theoretical evaluations of promising thienol [2,3-b]pyridine derivatives. J. Microbiol. Antimicrobials. 41(1):32-39.
7. Paccola, C C; Resende, C G; Stumpp, T; Miraglia, S M; Cipriano, I. The rat estrous cycle revisited: a quantitative and qualitative analysis. Anim. Reprod., v.10, n.4, p.677-683, October/December 2013.
8. Hild S A, Arrardi B J, Koduri A, Till B A, Reel J R. Effects of synthetic androgens on liver function using the rabbit as a model. Journal of Andrology, Vol. 31, No. 5, p. 472-481, September/October 2010.
9. Kumar N, Suvisaari J, Tsong Y, Aguillame C, Bardin C W, Lahteenmaki P, Sundaram K. Pharmacokinetics of 7α-methyl-19-nortestosterone in men and cynomolgus monkeys. Journal of Andrology, Vol. 18, No. 4, p. 352-358, July/August 1997.
10. Lemus A E, Enriquez J, Garcia G A, Grillasca I, Perez-Palacios G. 5α-reduction of norethisterone enhances its binding affinity for androgen receptors but diminishes its androgenic potency. J. Steroid Biochem, Molec. Blol., Vol. 60, No. 1-2, p. 121-129, 1997.
11. Bergirk E W, Janssen P S L, Turpun W, Van Der Vies J. Comparison of the receptor binding properties of nandrolone and testosterone under in vitro and in vivo conditions. J. Steroid Biochem. Vol. 22, No. 6, p. 831-836, 1985.
12. Pfaus J G. Pathways of Sexual Desire. J Sex Med 2009; 6:1506-1533.

What is claimed is:

1. A method of enhancing libido in an individual, including the steps of:
   administering a pharmaceutically effective amount of 0.05 mg to 1000 mg per day of a libido-enhancing therapeutic chosen from the group consisting of (5S, 10R,13S,17S)-13-methyl-3-oxohexadecahydro-1H-cyclopenta[a]phenanthren-17yl acetate (Formula I), (3S,5S,10R,13S,17S)-3-hydroxy-13-methylhexadecahydro-1H-cyclopenta[a]phenanthren-17yl acetate (Formula II), (5S,10S,13S,17S)-17-hydroxy-13-methyltetradecahydro-1H-cyclopenta[a]phenanthren-3(2H)-one (Formula III), and combinations thereof;

and enhancing libido in the individual.

2. The method of claim 1, wherein said administering step is further defined as administering the libido-enhancing therapeutic at a time chosen from the group consisting of once a day, multiple times a day, multiple days and at a time prior to sexual activity.

3. The method of claim 1, wherein the individual is at an age when libido and sexual desire have naturally decreased.

4. The method of claim 1, wherein said enhancing step occurs hours to weeks after said administering step.

5. The method of claim 1, further including the step of reducing the amount of androgenic side effects experienced with steroid administration.

6. The method of claim 1, wherein the individual is chosen from the group consisting of male humans, female humans, male animals, and female animals.

7. The method of claim 1, wherein said enhancing step further includes the step of reducing fatigue during sexual intercourse.

8. The method of claim 1, wherein said enhancing step further includes the step of sustaining libido for a period of time.

9. The method of claim 8, wherein said period of time is greater than seven hours.

10. A method of enhancing libido in an individual, including the steps of:

administering a pharmaceutically effective amount of 0.05 mg to 1000 mg per day of a libido-enhancing therapeutic chosen from the group consisting of (5S,10R,13S,17S)-13-methyl-3-oxohexadecahydro-1H-cyclopenta[a]phenanthren-17yl acetate (Formula I), (3S,5S,10R,13S,17S)-3-hydroxy-13-methylhexadecahydro-1H-cyclopenta[a]phenanthren-17yl acetate (Formula II), (5S,10S,13S,17S)-17-hydroxy-13-methyltetradecahydro-1H-cyclopenta[a]phenanthren-3(2H)-one (Formula III), and combinations thereof to the individual at an age when libido and sexual desire have naturally decreased;

and enhancing libido in the individual.

11. The method of claim 10, wherein said administering step is further defined as administering the libido-enhancing therapeutic to an individual at 40 years and above.

12. The method of claim 10, wherein said administering step is further defined as administering the libido-enhancing therapeutic to an individual at 50 years and above.

13. The method of claim 10, wherein said administering step is further defined as administering the libido-enhancing therapeutic to an individual at 60 years and above.

14. A method of enhancing libido and arousal, including the steps of:

administering a pharmaceutically effective amount of 0.05 mg to 1000 mg per day of a libido-enhancing therapeutic in combination with a sexual dysfunction therapeutic to an individual in need of an enhanced libido and arousal, wherein the libido-enhancing therapeutic is chosen from from the group consisting of (5S,10R,13S,17S)-13-methyl-3-oxohexadecahydro-1H-cyclopenta[a]phenanthren-17yl acetate (Formula I), (3S,5S,10R,13S,17S)-3-hydroxy-13-methylhexadecahydro-1H-cyclopenta[a]phenanthren-17yl acetate (Formula II), (5S,10S,13S,17S)-17-hydroxy-13-methyltetradecahydro-1H-cyclopenta[a]phenanthren-3(2H)-one (Formula III), and combinations thereof; and enhancing libido and arousal in the individual.

15. The method of claim 14, wherein the sexual dysfunction therapeutic is chosen from the group consisting of sildenafil, tadalafil, vardenafil, avanafil, bremelanotide, and alprostadil.

16. The method of claim 1, further including the step of stabilizing the therapeutic through an acetate group of the therapeutic and providing increased absorption and distribution in the body.

17. A method of enhancing libido in an individual, including the step of:

administering a therapeutic compound that enhances libido without producing androgenic side effects in an amount of 0.05 mg to 1000 mg per day.

18. The method of claim 17, wherein the therapeutic compound is chosen from the group consisting of (5S,10R,13S,17S)-13-methyl-3-oxohexadecahydro-1H-cyclopenta[a]phenanthren-17yl acetate (Formula I), (3S,5S,10R,13S,17S)-3-hydroxy-13-methylhexadecahydro-1H-cyclopenta[a]phenanthren-17yl acetate (Formula II), (5S,10S,13S,17S)-17-hydroxy-13-methyltetradecahydro-1H-cyclopenta[a]phenanthren-3(2H)-one (Formula III), and combinations thereof.

* * * * *